(12) United States Patent
Kubo

(10) Patent No.: US 7,329,880 B2
(45) Date of Patent: Feb. 12, 2008

(54) MULTIPHOTON-EXCITATION LASER SCANNING MICROSCOPE

(75) Inventor: Hirokazu Kubo, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/407,300

(22) Filed: Apr. 19, 2006

(65) Prior Publication Data

US 2006/0237666 A1 Oct. 26, 2006

(30) Foreign Application Priority Data

Apr. 25, 2005 (JP) ............................ 2005-126592
Feb. 23, 2006 (JP) ............................ 2006-046768

(51) Int. Cl.
*G01T 1/20* (2006.01)

(52) U.S. Cl. .................................. 250/458.1

(58) Field of Classification Search ............ 250/458.1, 250/363.01, 367, 368, 369, 361 C
See application file for complete search history.

(56) References Cited

U.S. PATENT DOCUMENTS

| | | | |
|---|---|---|---|
| 6,485,413 B1* | 11/2002 | Boppart et al. | 600/160 |
| 6,796,699 B2* | 9/2004 | Birk et al. | 362/556 |
| 6,848,825 B1* | 2/2005 | Simon et al. | 374/141 |
| 6,898,367 B2 | 5/2005 | Birk et al. | |
| 7,015,444 B2* | 3/2006 | Kawano et al. | 250/201.3 |
| 2004/0190134 A1* | 9/2004 | Tahara et al. | 359/386 |
| 2005/0263690 A1* | 12/2005 | Araya et al. | 250/234 |
| 2006/0045163 A1* | 3/2006 | Chuang et al. | 372/100 |

FOREIGN PATENT DOCUMENTS

| | | | |
|---|---|---|---|
| JP | 2000206415 A | * | 7/2000 |
| JP | 2002-243641 A | | 2/2002 |
| JP | 2002-98896 A | | 4/2002 |
| JP | 2003-028795 A | | 1/2003 |
| JP | 2005257507 A | * | 9/2005 |
| JP | 2005257509 A | * | 9/2005 |

\* cited by examiner

*Primary Examiner*—David Porta
*Assistant Examiner*—David S Baker
(74) *Attorney, Agent, or Firm*—Frishauf, Holtz, Goodman & Chick, P.C.

(57) ABSTRACT

A compact and inexpensive multiphoton-excitation laser scanning microscope for observing fluorescence by multiphoton excitation having a plurality of wavelengths by irradiating a specimen with ultrashort pulsed laser light having a plurality of wavelengths is provided. A multiphoton-excitation laser scanning microscope includes a laser light source that emits ultrashort pulsed laser light with a single wavelength, an optical fiber into which the ultrashort pulsed laser light from the laser light source is introduced and which broadens the spectrum of the ultrashort pulsed laser light, a laser scanning unit that scans the spectrally broadened ultrashort pulsed laser light emitted from the optical fiber, an objective optical system that focuses the scanned ultrashort pulsed laser light onto a specimen, optical detectors that detect fluorescence by multiphoton excitation emitted from the focal position of the ultrashort pulsed laser light in the specimen, and a dispersion-compensating optical system that compensates for the group velocity dispersion of the entire microscope that influences the pulse width of the ultrashort pulsed laser light.

7 Claims, 8 Drawing Sheets

MULTIPHOTON-EXCITATION LASER SCANNING MICROSCOPE

BACKGROUND OF THE INVENTION

1. Field of the Invention

The present invention relates to a multiphoton-excitation laser scanning microscope.

This application is based on Japanese Patent Applications Nos. 2005-126592 and 2006-46768, the content of which is incorporated herein by reference.

2. Description of Related Art

Known apparatuses in the related art for observing cellular function and the like by irradiating the surface of a specimen, such as a living organism, with ultrashort pulsed laser light and detecting fluorescence by multiphoton-excitation generated from a comparatively deep position below the surface of the specimen include a multiphoton-excitation-type examination apparatus (see, for example, Japanese Unexamined Patent Application Publication No. 2002-243641).

When different types of fluorescence by multiphoton-excitation are observed by irradiating ultrashort pulsed laser light having different wavelengths, this multiphoton-excitation-type examination apparatuses must use a light source that can emit wavelength-tunable ultrashort pulsed laser light or a plurality of light sources that emit ultrashort pulsed laser light with a single wavelength.

On the other hand, known confocal laser scanning microscopes include an apparatus in which femtosecond-order ultrashort pulsed laser light is introduced into a microstructured optical element, such as a photonic bandgap material, thereby spectrally broadening the laser light to emit laser light having a wide wavelength band; the wavelength range is selected using an acousto-optical filter (AOTF), a prism, or a grating (see, for example, U.S. Pat. Nos. 6,796,699 and 6,898,367).

BRIEF SUMMARY OF THE INVENTION

The present invention provides a compact and inexpensive multiphoton-excitation laser scanning microscope for observing fluorescence by multiphoton-excitation having a plurality of wavelengths by irradiating a specimen with ultrashort pulsed laser light having a plurality of wavelengths.

In order to achieve the object described above, the present invention provides the following solutions.

According to a first aspect, the present invention provides a multiphoton-excitation laser scanning microscope including a laser light source that emits ultrashort pulsed laser light with a single wavelength, an optical fiber into which the ultrashort pulsed laser light from the laser light source is introduced and which broadens the spectrum of the ultrashort pulsed laser light, a laser scanning unit that scans the spectrally broadened ultrashort pulsed laser light emitted from the optical fiber, an objective optical system that focuses the ultrashort pulsed laser light scanned by the laser scanning unit onto a specimen, optical detectors that detect fluorescence by multiphoton-excitation emitted from the focal position of the ultrashort pulsed laser light in the specimen, and a dispersion-compensating optical system that compensates for the group velocity dispersion of the entire microscope that influences to the pulse width of the ultrashort pulsed laser light.

According to the first aspect of the present invention, when the ultrashort pulsed laser light with a single wavelength emitted from the laser light source is introduced into the optical fiber, the ultrashort pulsed laser light is spectrally broadened while propagating in the optical fiber and is emitted as ultrashort pulsed laser light having a wide wavelength band. The ultrashort pulsed laser light emitted from the optical fiber is scanned by the laser scanning unit and is focused onto the specimen by the objective optical system. In addition, the operation of the dispersion-compensating optical system can compensate for an increase in the pulse width caused by the dispersion of the entire microscope. Thus, fluorescence by multiphoton-excitation is generated at the focal position in the specimen by an efficient multiphoton-excitation effect. By detecting this fluorescence with the optical detectors, the internal state of the specimen at a predetermined position in the depth direction can be observed as a fluorescence image.

In this case, by allowing the ultrashort pulsed laser light having the wide wavelength band emitted from the optical fiber to be incident on the specimen without selecting the wavelength, a plurality of fluorescent substances can be excited at the same time and a plurality of types of fluorescence by multiphoton-excitation having different wavelengths can be generated at the same time. Furthermore, by cutting out ultrashort pulsed laser light having a predetermined wavelength band from the ultrashort pulsed laser light having the wide wavelength band, fluorescence by multiphoton-excitation having a desired wavelength can also be generated.

According to the first aspect of the present invention, the multiphoton-excitation laser scanning microscope preferably includes a wavelength-selecting optical system that selects the wavelength of the spectrally broadened ultrashort pulsed laser light emitted from the optical fiber.

In this structure, the specimen can be irradiated with ultrashort pulsed laser light having a predetermined wavelength by the operation of the wavelength-selecting optical system. In particular, by setting the wavelength selection by the wavelength-selecting optical system to be variable, ultrashort pulsed laser light having an appropriate wavelength can be made incident on the specimen according to the fluorescent substance in the specimen.

According to the first aspect of the present invention, the multiphoton-excitation laser scanning microscope preferably includes a spectrum detecting unit that detects the center wavelength of the ultrashort pulsed laser light whose wavelength is selected by the wavelength-selecting optical system, and an adjusting unit that adjusts the amount of dispersion compensation of the dispersion-compensating optical system on the basis of the center wavelength detected by the spectrum detecting unit.

In this structure, the amount of dispersion compensation of the dispersion-compensating optical system can be adjusted by the operation of the adjusting unit according to the center wavelength of the ultrashort pulsed laser light obtained as a result of the wavelength selection by the wavelength-selecting optical system. Thereby, an increase in the pulse width, which is different for each wavelength, caused by the dispersion of the entire microscope can be compensated for and the multiphoton-excitation effect can be efficiently generated in the specimen.

According to a second aspect, the present invention provides a multiphoton-excitation laser scanning microscope including a laser light source that emits ultrashort pulsed laser light with a single wavelength, an optical fiber into which the ultrashort pulsed laser light from the laser light source is introduced and which broadens the spectrum of the ultrashort pulsed laser light, a wavelength-selecting optical system that selectively separates ultrashort pulsed laser light having a predetermined wavelength from the spectrally broadened ultrashort pulsed laser light emitted from the optical fiber, a laser scanning unit that scans the remaining ultrashort pulsed laser light from which the ultrashort pulsed laser light having the predetermined wavelength is separated by the wavelength-selecting optical system, a multiplexer that multiplexes the ultrashort pulsed laser light having the predetermined wavelength with the remaining ultrashort pulsed laser light scanned by the laser scanning unit, an objective optical system that focuses the ultrashort pulsed laser light multiplexed by the multiplexer onto a specimen, and optical detectors that detect fluorescence by multiphoton-excitation emitted from the focal position of the ultrashort pulsed laser light in the specimen.

According to the second aspect of the present invention, when the ultrashort pulsed laser light with a single wavelength emitted from the laser light source is introduced into the optical fiber, the ultrashort pulsed laser light is spectrally broadened while propagating in the optical fiber and is emitted as ultrashort pulsed laser light having a wide wavelength band. The ultrashort pulsed laser light that has been spectrally broadened passes through the wavelength-selecting optical system. Thereby ultrashort pulsed laser light having a predetermined wavelength is selectively separated. The remaining ultrashort pulsed laser light from which the ultrashort pulsed laser light having the predetermined wavelength is separated is scanned by the laser scanning unit, and is focused onto the specimen by the objective optical system. Thus, fluorescence by multiphoton-excitation is generated at the focal position in the specimen by the multiphoton-excitation effect. By detecting this fluorescence with the optical detectors, the internal state of the specimen at a predetermined position in the depth direction can be observed as a fluorescence image.

Furthermore, since the ultrashort pulsed laser light that is separated by the wavelength-selecting optical system and that has the predetermined wavelength is multiplexed with the multiplexer with the ultrashort pulsed laser light that remains after scanning, the ultrashort pulsed laser light having the predetermined wavelength is irradiated at a specific position of the specimen. Thus, the state of the specimen can be observed as a fluorescence by multiphoton-excitation image while multiphoton excitation stimulation by the ultrashort pulsed laser light having the predetermined wavelength is provided at the specific position of the specimen.

According to the second aspect of the present invention, the multiphoton-excitation laser scanning microscope may include a spectrum detecting unit that detects the center wavelength of the ultrashort pulsed laser light having the predetermined wavelength separated by the wavelength-selecting optical system, and a wavelength-adjusting unit that adjusts the wavelength of the ultrashort pulsed laser light to be separated by the wavelength-selecting optical system on the basis of the center wavelength detected by the spectrum detecting unit.

In this structure, the wavelength-adjusting unit adjusts the wavelength of the ultrashort pulsed laser light separated on the basis of the center wavelength detected by the spectrum detecting unit. Consequently, highly accurate multiphoton excitation stimulation can be performed using the ultrashort pulsed laser light having the predetermined wavelength, which is accurately selected.

According to the second aspect of the present invention, the multiphoton-excitation laser scanning microscope may include a dispersion-compensating optical system that compensates for the group velocity of the entire microscope that influences the pulse width of dispersion with respect to the ultrashort pulsed laser light having the predetermined wavelength separated by the wavelength-selecting optical system, and a dispersion-compensation adjusting unit that adjusts the amount of dispersion compensation of the dispersion-compensating optical system on the basis of the center wavelength detected by the spectrum detecting unit.

In this structure, the group velocity dispersion of the entire microscope that influences the pulse width of the ultrashort pulsed laser light with the predetermined wavelength, which is separated by the wavelength-selecting optical system, is compensated for by the dispersion-compensating optical system on the basis of the center wavelength detected by the spectrum detecting unit. Thereby, an increase in the pulse width, which is different for each wavelength, caused by the dispersion of the entire microscope can be compensated for, and highly accurate stimulation by multiphoton excitation can be performed.

According to the second aspect of the present invention, the multiphoton-excitation laser scanning microscope may include a second laser scanning unit that scans the ultrashort pulsed laser light having the predetermined wavelength separated by the wavelength-selecting optical system.

According to each of the aspects of the present invention, the multiphoton-excitation laser scanning microscope may include a peak-intensity-adjusting optical system disposed between the laser light source and the optical fiber, the peak-intensity-adjusting optical system adjusting the peak intensity of the ultrashort pulsed laser light to be introduced into the optical fiber.

Further features, advantages, and the like of the present invention will become apparent from the description of the following embodiments and the attached drawings.

DETAILED DESCRIPTION OF THE INVENTION

A multiphoton-excitation laser scanning microscope according to a first embodiment of the present invention will now be described with reference to FIG. 1.

Figure 1:
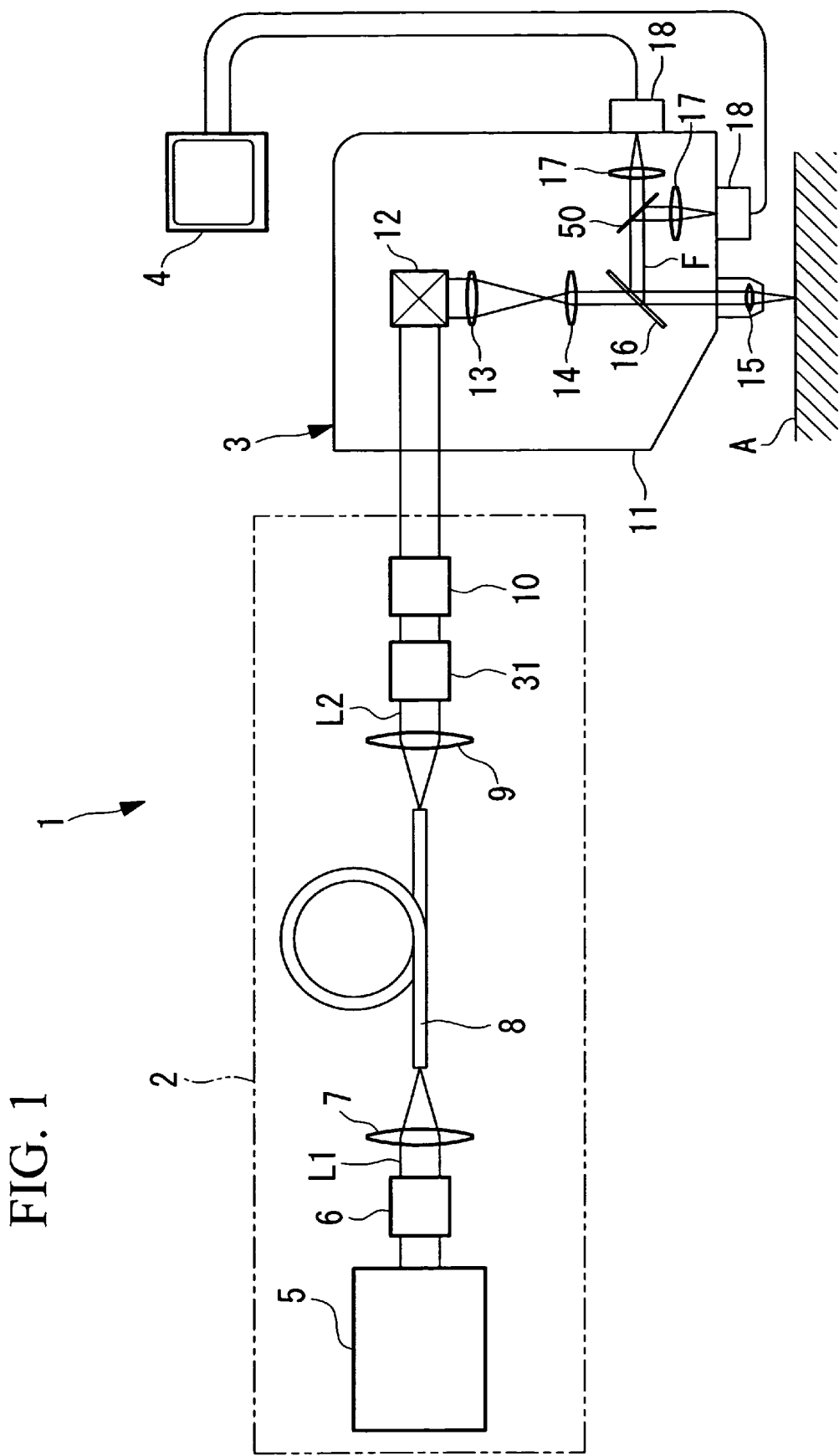
FIG. 1 is an overall structural diagram showing a multiphoton-excitation laser scanning microscope according to a first embodiment of the present invention.

As shown in FIG. 1, a multiphoton-excitation laser scanning microscope 1 of this embodiment includes an illumination unit 2, a microscope unit 3, and an image display unit 4.

As shown in FIG. 1, the illumination unit 2 of this embodiment includes a laser light source 5 that emits the ultrashort pulsed laser light L1 having the pulse width from picosecond-order to femtosecond-order, an alignment-adjusting optical system 6 that adjusts the position and the angle of the optical axis of the ultrashort pulsed laser light L1 emitted from the laser light source 5, a coupling optical system 7 that focuses the alignment-adjusted ultrashort pulsed laser light L1, an optical fiber 8 composed of a photonic bandgap material, one end of which is disposed at the focal position of the coupling optical system 7, a collimator optical system 9 that converts ultrashort pulsed laser light L2 emitted from the optical fiber 8 into substantially collimated light, and a beam-shaping optical system 10 that adjusts the beam diameter and the divergence of the substantially collimated laser light L2. A dispersion-compensating optical system 31 that compensates for the group velocity dispersion of the entire microscope that influences the pulse width of the ultrashort pulsed laser light L2 is provided in front of the beam-shaping optical system 10.

The laser light source 5 emits, for example, ultrashort pulsed laser light L1 having a wavelength of 800 nm.

The alignment-adjusting optical system 6 includes, for example, two reflective mirrors whose angles of inclination can be adjusted in two axes perpendicular to the optical axis, and a beam position-detecting optical system. Thereby, the alignment-adjusting optical system 6 can adjust the central position of the light flux of the ultrashort pulsed laser light L1 emitted from the laser light source 5 so as to be aligned with the incident optical axis of the optical fiber 8.

The optical fiber 8 is composed of, for example, a photonic crystal fiber or a tapered fiber. Thereby, the optical fiber 8 spectrally broadens the ultrashort pulsed laser light L1 with a wavelength of 800 nm that is introduced into an end thereof while the ultrashort pulsed laser light L1 propagates therein, and emits the ultrashort pulsed laser light L2, which is white light having a spectral bandwidth of about 300 to 1,600 nm, from the other end.

The beam-shaping optical system 10 is composed of, for example, a Galilean beam expander combining a biconvex lens and a plano-concave lens. Thereby, the beam-shaping optical system 10 compensates for the beam diameter and the divergence of the ultrashort pulsed laser light L2 introduced into the microscope unit such that the beam diameter is substantially the same as the pupil diameter of an objective lens 15 at the entrance pupil position of the objective lens 15.

The microscope unit 3 includes a housing 11, a scanner 12, a pupil-projection lens 13, an imaging lens 14, an objective lens 15, a dichroic mirror 16, a wavelength-selecting element (wavelength-selecting optical system) 50, a focusing lens 17, and optical detectors 18. The scanner 12 two-dimensionally scans the white ultrashort pulsed laser light L2, which is formed of substantially collimated light emitted from the illumination unit 2. The pupil-projection lens 13 focuses the scanned ultrashort pulsed laser light L2 to form an intermediate image. The imaging lens 14 collects the ultrashort pulsed laser light that has formed the intermediate image. The objective lens 15 focuses the ultrashort pulsed laser light L2 emitted from the imaging lens 14 to re-image the laser light onto a specimen A. The dichroic mirror 16 splits off from the ultrashort pulsed laser light L2 fluorescence by multiphoton-exitation F that is generated in the specimen A and that is collected by the objective lens 15. The wavelength-selecting element (wavelength-selecting optical system) 50 selects the wavelength of the split-off fluorescence by multiphoton excitation. The optical detectors 18 image the fluorescence F.

The scanner 12 is composed of, for example, proximity galvano mirrors in which two galvano mirrors (not shown in the drawing) that can rock around two mutually orthogonal axes are disposed close to each other.

Each of the optical detectors 18 is, for example, a photomultiplier tube (PMT). A plurality of optical detectors 18, for example, two optical detectors 18, are provided. The wavelength-selecting optical system 50 is, for example, composed of a dichroic mirror, a grating with slits, or a combination thereof. For example, when a specimen is stained with different fluorescent dyes to allow fluorescence to be generated in different wavelengths, the fluorescence is separated with the wavelength-selecting element 50, and thus fluorescence having different wavelengths generated from different fluorescent dyes can be separately detected.

The image display unit 4 displays a fluorescence image formed on the basis of the fluorescence F by multiphoton excitation from the specimen A detected by the optical detectors 18.

The operation of the multiphoton-excitation laser scanning microscope 1 of this embodiment, having the above structure, will be described below.

The laser light source 5 emits the ultrashort pulsed laser light L1. The position and the angle of the optical axis of the ultrashort pulsed laser light L1 are adjusted by the alignment-adjusting optical system 6. The ultrashort pulsed laser light L1 is then focused by the coupling optical system 7 and is introduced into one end of the optical fiber 8.

The ultrashort pulsed laser light L1 introduced into the optical fiber 8 is spectrally broadened by a nonlinear effect in of the optical fiber 8 composed of a photonic bandgap material, and is emitted from the other end of the optical fiber 8 as white ultrashort pulsed laser light L2 having a wide spectral bandwidth of 300 to 1,600 nm. The emitted white ultrashort pulsed laser light L2 is converted to substantially collimated light by the collimator optical system 9 and is then emitted toward the microscope unit 3 in a state in which the beam diameter and the divergence are adjusted by the beam-shaping optical system 10.

The ultrashort pulsed laser light L2 introduced into the microscope unit 3 is focused at a predetermined depth in the specimen A through the pupil-projection lens 13, the imaging lens 14, the dichroic mirror 16, which cuts the spectral range band of the fluorescence, and the objective lens 15 while being two-dimensionally scanned by the scanner 12, and generates a multiphoton-excitation effect at that position.

Since the position and the angle of the optical axis of the ultrashort pulsed laser light L2 are adjusted by the alignment-adjusting optical system 6 and the beam diameter and the divergence of the ultrashort pulsed laser light L2 are also adjusted by the beam-shaping optical system 10, the ultrashort pulsed laser light L2 can be focused at a predetermined depth in the specimen A with high accuracy. Consequently, bright fluorescence images by multiphoton-exitation with high spatial resolution can be obtained.

Furthermore, in the ultrashort pulsed laser light L2, the group velocity dispersion of the entire microscope is compensated for by the operation of the dispersion-compensating optical system 31. Thereby, an increase in the pulse width can be compensated for and a multiphoton-excitation effect can be efficiently generated at the focal position of the specimen A.

According to the multiphoton-excitation laser scanning microscope 1 of this embodiment, the white ultrashort pulsed laser light L2 is focused on the specimen A. Therefore, when a plurality of fluorescent substances are contained in the specimen A, different types of fluorescence by multiphoton-exitation F having a plurality of wavelengths can be generated at the same time by ultrashort pulsed laser light of a plurality of spectral range that are included in the white ultrashort pulsed laser light L2.

According to the multiphoton-excitation laser scanning microscope 1 of this embodiment, such an effect can be achieved with a compact laser light source 5 that can emit only the ultrashort pulsed laser light L1 having a single wavelength (800 nm). Therefore, a large expensive wavelength-tunable laser light source need not be used, resulting in an advantage in that the size and cost of the multiphoton-excitation laser scanning microscope 1 can be reduced.

Figure 2:
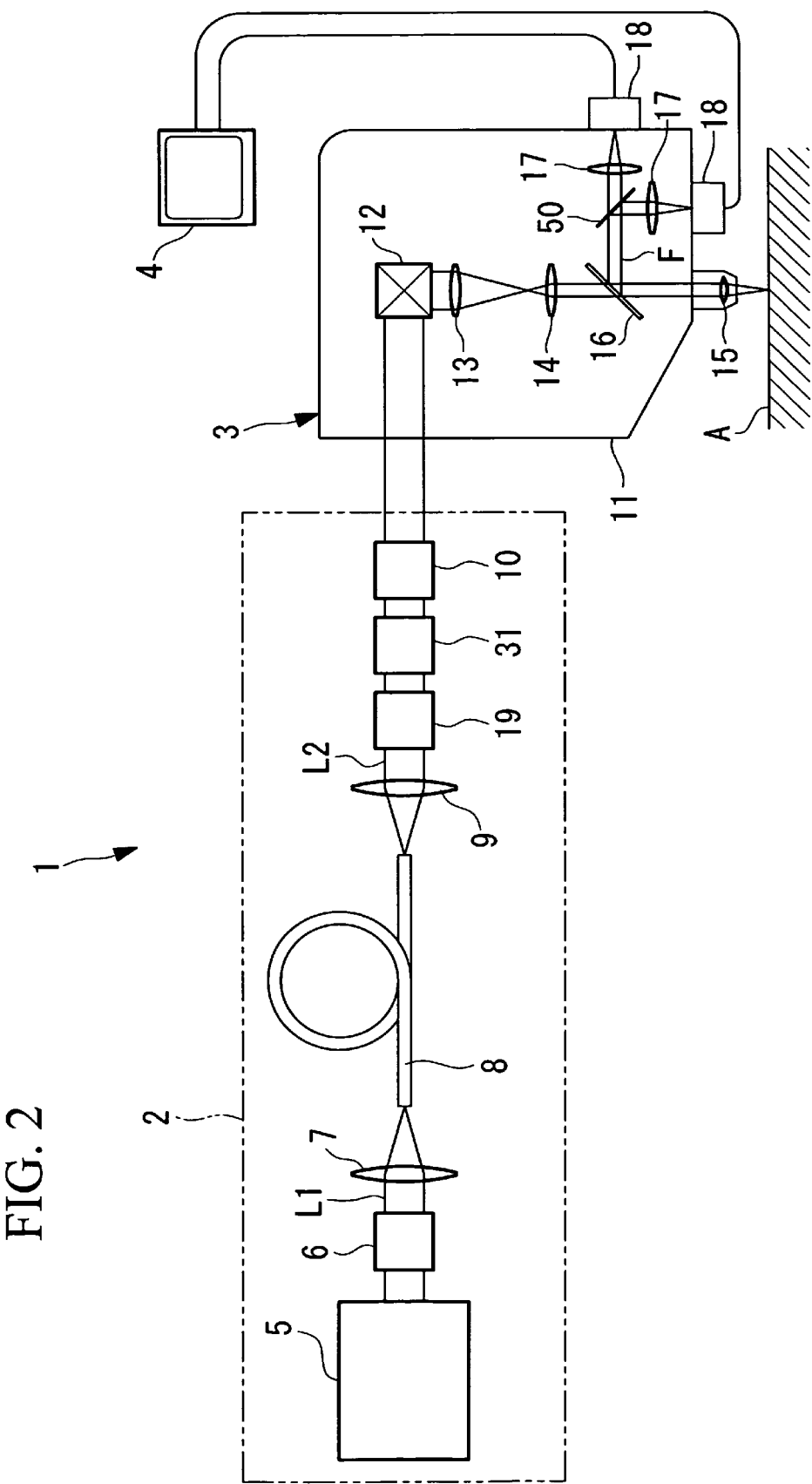
FIG. 2 is an overall structural diagram showing a modification of the multiphoton-excitation laser scanning microscope in FIG. 1.

In the multiphoton-excitation laser scanning microscope 1 of this embodiment, the white ultrashort pulsed laser light L2 emitted from the optical fiber 8 is directly subjected to beam shaping by the beam-shaping optical system 10, and is introduced into the microscope unit 3. Alternatively, as shown in FIG. 2, a color filter or a bandpass filter 19 that limits the spectrum range of the ultrashort pulsed laser light L2 to be introduced into the microscope unit 3 may be provided. This structure allows the ultrashort pulsed laser light L2 not containing unnecessary light to be introduced into the microscope unit 3, and thus noise can be reduced and fluorescence images by multiphoton-exitation with high resolution can be obtained.

Figure 3:
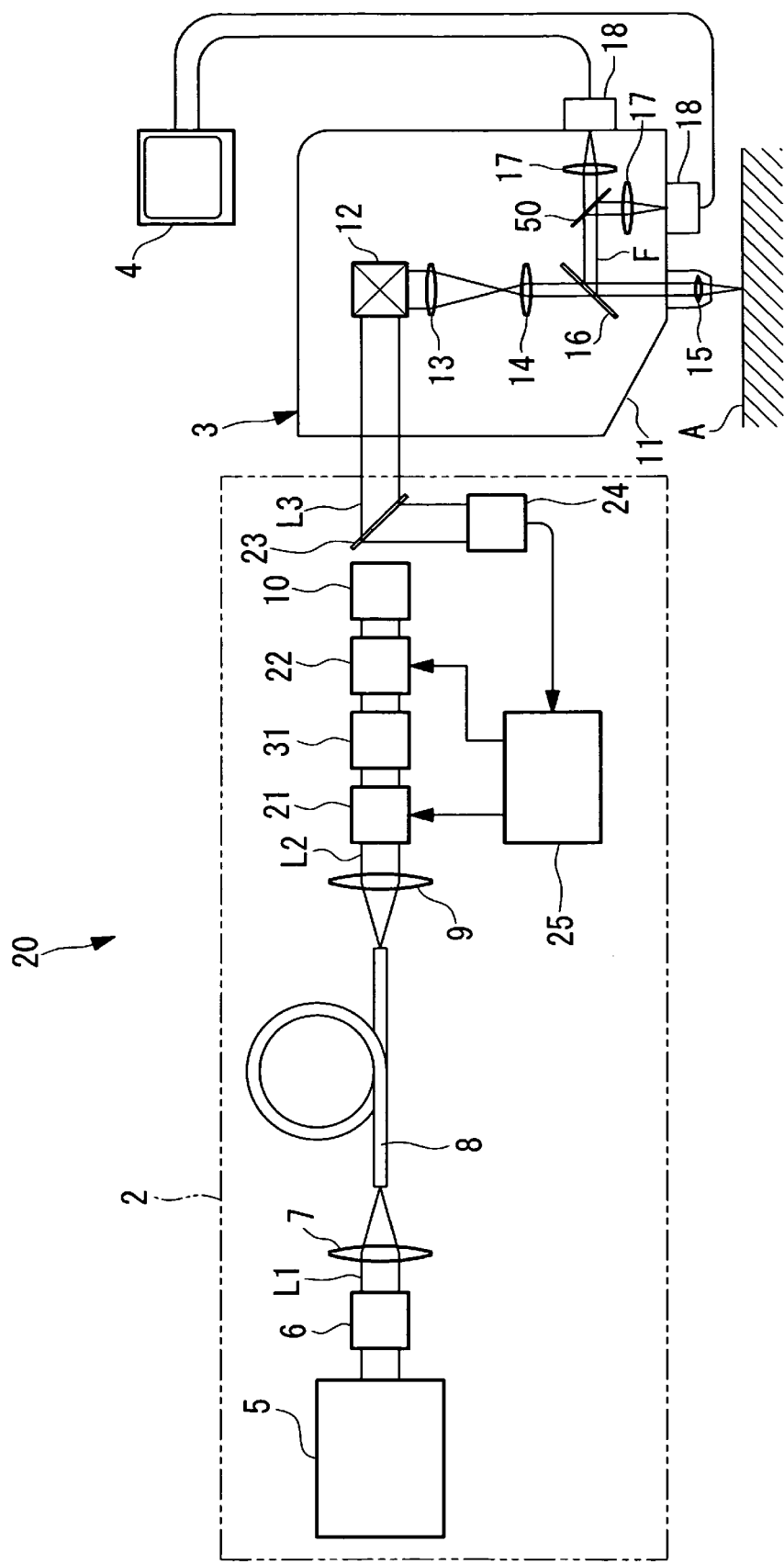
FIG. 3 is an overall structural diagram showing a multiphoton-excitation laser scanning microscope according to a second embodiment of the present invention.

A multiphoton-excitation laser scanning microscope 20 according to a second embodiment of the present invention will now be described with reference to FIG. 3.

In the description of this embodiment, components that are common to those of the above-described multiphoton-excitation laser scanning microscope 1 of the first embodiment have the same reference numerals, and a description of the common structure is omitted.

A multiphoton-excitation laser scanning microscope 20 of this embodiment includes a wavelength-selecting optical system 21 and an intensity-adjusting optical system 22, which are disposed between the collimator optical system 9 and the beam-shaping optical system 10. The wavelength-selecting optical system 21 adjusts the spectral range and the bandwidth of the white ultrashort pulsed laser light L2 emitted from the collimator optical system 9. The intensity-adjusting optical system 22 adjusts the intensity of the ultrashort pulsed laser light L2.

Examples of the wavelength-selecting optical system 21 include acousto-optical elements such as an acousto-optical tunable filter (AOTF), an acousto-optical modulator (AOM), and an acousto-optical beam splitter (AOBS); electro-optical elements such as an electro-optical modulator (EOM); filters such as a color filter, a bandpass filter, and a bypass filter; a grating with slits; a prism with slits; an etalon with slits; and an achromatic lens having a large axial aberration with a pin hole.

Examples of the intensity-adjusting optical system 22 include acousto-optical elements such as an AOTF, an AOM, and an AOBS; electro-optical elements such an EOM; a polarizing plate; a variable neutral density (ND) filter; and a variable aperture.

The multiphoton-excitation laser scanning microscope 20 also includes a beam sampler 23, a spectrometer 24, and a control unit 25, which are disposed between the beam-shaping optical system 10 and the microscope unit 3. The beam sampler 23 splits off part of the ultrashort pulsed laser light L2 passing through the beam-shaping optical system 10. The spectrometer 24 detects the center wavelength and the spectrum of the split-off ultrashort pulsed laser light L2. The control unit 25 controls the wavelength-selecting optical system 21 and the intensity-adjusting optical system 22 on the basis of the detected center wavelength, the spectral bandwidth and intensity of the ultrashort pulsed laser light L2.

According to the multiphoton-excitation laser scanning microscope 20 of this embodiment, the control unit 25 sets the center wavelength, the spectral bandwidth and intensity of ultrashort pulsed laser light L3 that is irradiated on the specimen A, thereby setting the center wavelength and the spectral bandwidth of the ultrashort pulsed laser light L3 cut from the white ultrashort pulsed laser light L2 by the operation of the wavelength-selecting optical system 21. In addition, the intensity of the cut out ultrashort pulsed laser light L3 is set by the operation of the intensity-adjusting optical system 22.

According to this embodiment, the ultrashort pulsed laser light L3 emitted from the beam-shaping optical system 10 is spectrally separated with the spectrometer 24, and the obtained center wavelength and the spectrum are sent to the control unit 25. Accordingly, the control unit 25 feeds back the center wavelength, the spectral bandwidth and intensity of the ultrashort pulsed laser light L3 from the beam-shaping optical system 10 to the wavelength-selecting optical system 21 and the intensity-adjusting optical system 22. Thus, the ultrashort pulsed laser light L3 having a desired center wavelength, spectral bandwidth and intensity can be introduced into the microscope unit 3.

Figure 4:
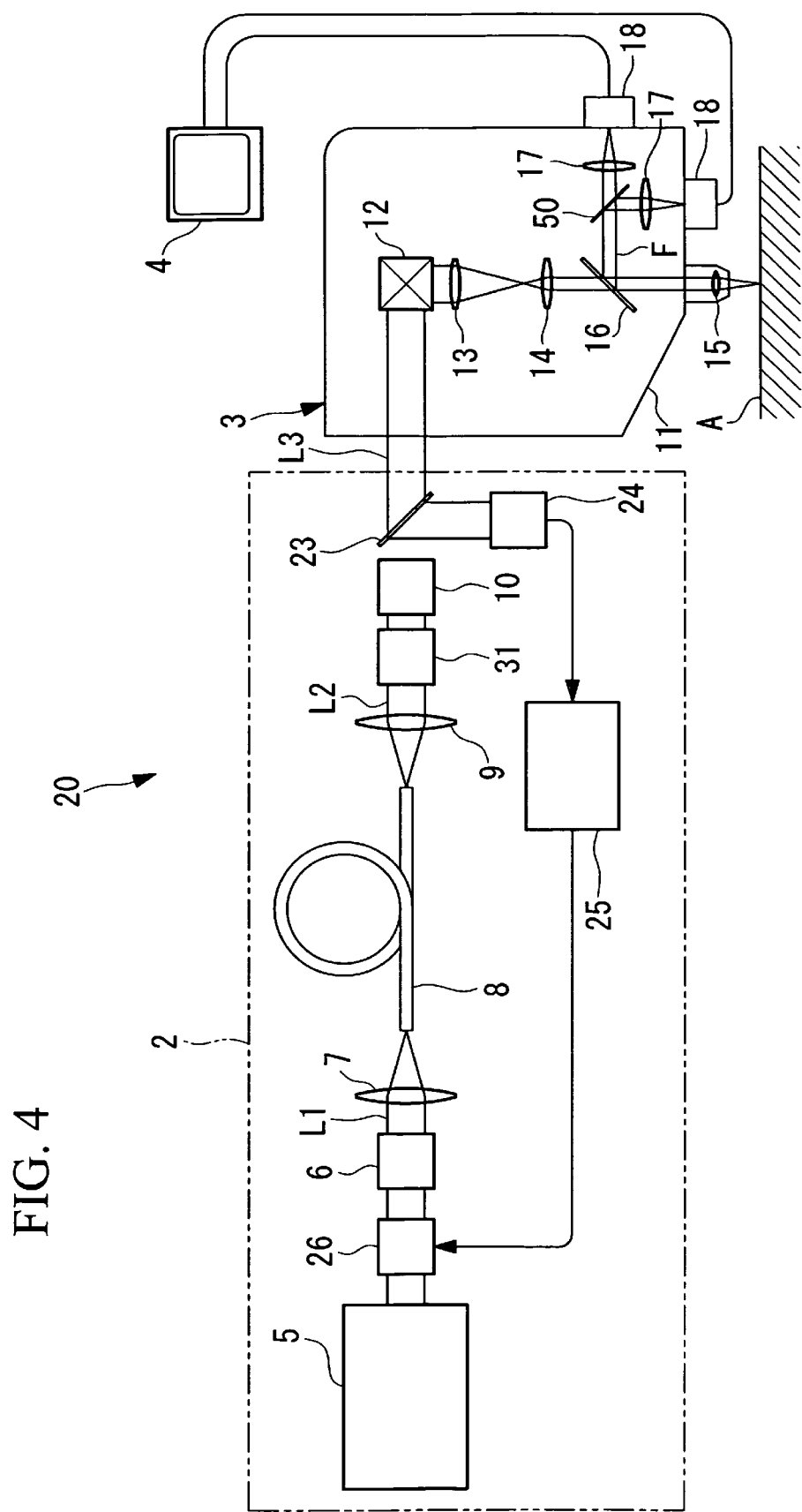
FIG. 4 is an overall structural diagram showing a modification of the multiphoton-excitation laser scanning microscope in FIG. 3.

In the multiphoton-excitation laser scanning microscope 20 of this embodiment, the wavelength-selecting optical system 21 and the intensity-adjusting optical system 22 are provided between the collimator optical system 9 and the beam-shaping optical system 10, thereby adjusting the center wavelength, the spectral bandwidth and intensity of the white ultrashort pulsed laser light L2, which is spectrally broadened upon passing through the optical fiber 8. Alternatively, as shown in FIG. 4, an output-adjusting optical system 26 may be provided before the light is introduced into the optical fiber 8 so as to control the peak intensity of the ultrashort pulsed laser light L1 introduced into the optical fiber 8. Thus, the center wavelength, the spectral bandwidth and intensity of the ultrashort pulsed laser light L2 may be adjusted.

This structure uses the phenomenon that the intensity of the nonlinear effect generated in the optical fiber 8 varies depending on the peak intensity of the ultrashort pulsed laser light. Methods for adjusting the peak intensity include a method of decreasing the integrated intensity (power) of the ultrashort pulsed laser light and a method of changing the pulse width without changing the integrated intensity (power). In order to decrease the integrated intensity (power), the same elements as those (such as acousto-optical elements and a variable ND filter) used in the above-described intensity-adjusting optical system 22 can be used.

Figure 5:
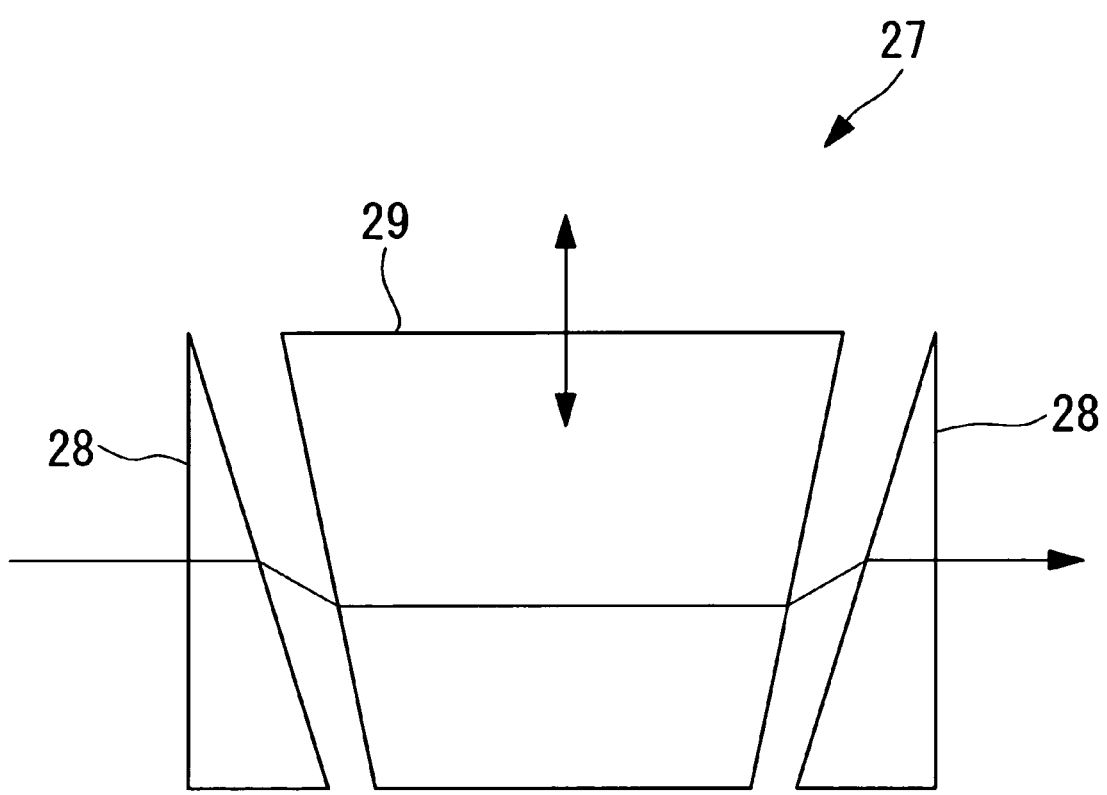
FIG. 5 is a schematic view showing an example of a dispersive optical element used in a second modification of the multiphoton-excitation laser scanning microscope in FIG. 3.

In order to change the pulse width while maintaining the power, a pulse width-adjusting optical system composed of a pair of prisms, a pair of gratings, or a dispersive element 27, for example is disposed as the peak intensity-adjusting optical system 26 to control the pulse width of the ultrashort pulsed laser light L1. Thus, the center wavelength, the spectral bandwidth and intensity of the ultrashort pulsed laser light L2 are adjusted. As shown in FIG. 5, an example of the dispersive element 27 is an element in which a pair of triangular prisms 28 and a trapezoidal prism 29 are aligned and the trapezoidal prism 29 is moved in the direction intersecting with the optical axis.

Figure 6:
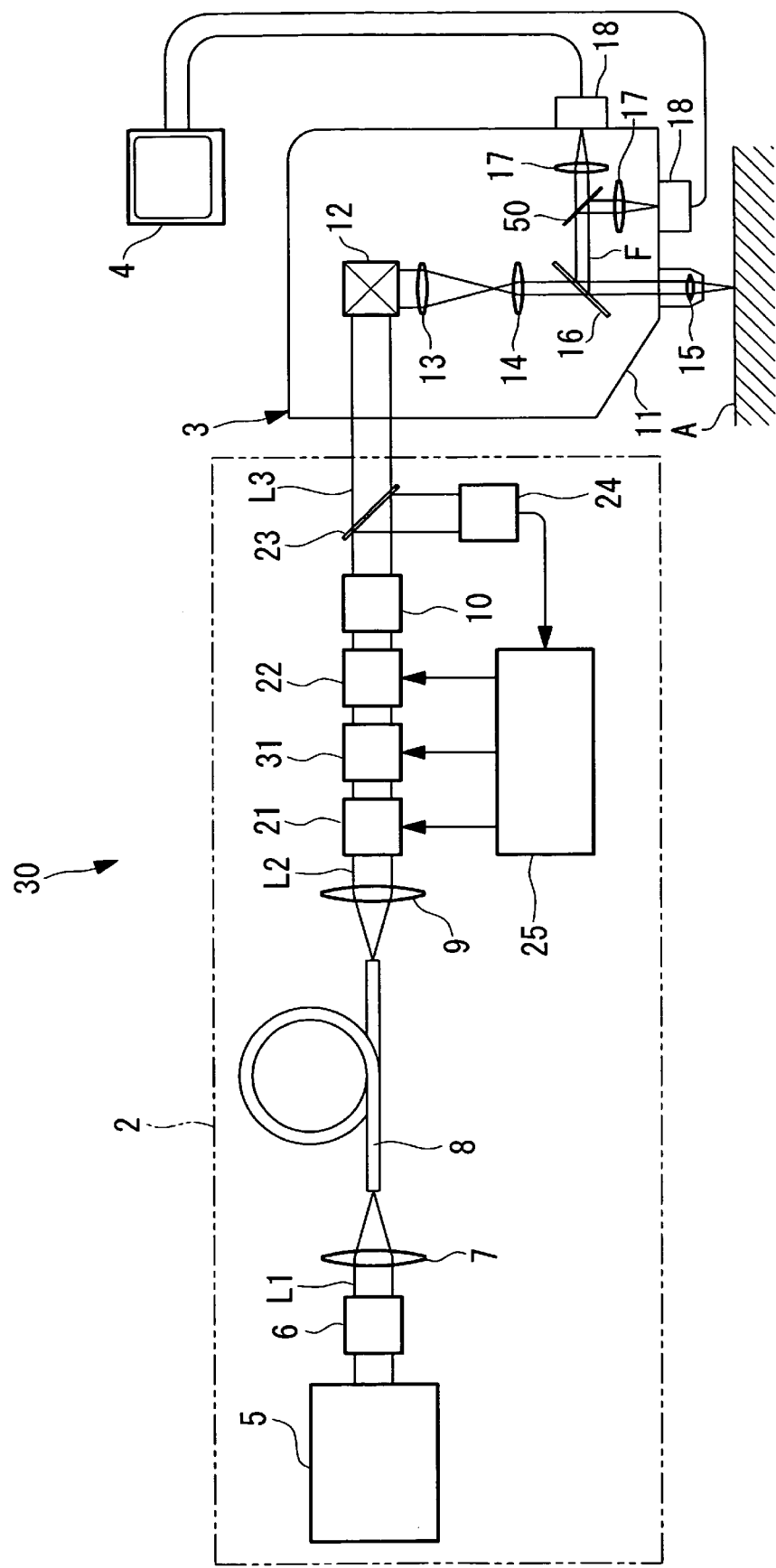
FIG. 6 is an overall structural diagram showing a multiphoton-excitation laser scanning microscope according to a third embodiment of the present invention.

A multiphoton-excitation laser scanning microscope 30 according to a third embodiment of the present invention will now be described with reference to FIG. 6.

In the description of this embodiment, components that are common to those of the above-described multiphoton-excitation laser scanning microscope 20 of the second embodiment have the same reference numerals, and a description of the common structure is omitted.

In a multiphoton-excitation laser scanning microscope 30 according to this embodiment, a dispersion-compensating optical system 31 is provided behind the wavelength-selecting optical system 21. The dispersion-compensating optical system 31 compensates for the group velocity dispersion of the entire microscope that influences the pulse width of the ultrashort pulsed laser light L3 that has bandwidth that is cut out by the wavelength-selecting optical system 21.

The dispersion-compensating optical system 31 is composed of a pair of prisms or a pair of gratings. The amount of dispersion compensation can be controlled by controlling the distance between the prisms or the distance between the gratings.

In this embodiment, the control unit 25 is also connected to the dispersion-compensating optical system 31. The control unit 25 controls the dispersion-compensating optical system 31 on the basis of the center wavelength of the ultrashort pulsed laser light L3 emitted from the beam-shaping optical system 10 so as to provide the distance between the prisms or the distance between the gratings for each wavelength for compensating for the dispersion of the entire microscope, the distance being recorded in a memory unit (not shown in the figure) in advance.

With the multiphoton-excitation laser scanning microscope 30 of this embodiment, having the above structure, the group velocity dispersion for each wavelength is compensated for by the operation of the dispersion-compensating optical system 31 to optimize the pulse width of the ultrashort pulsed laser light L3 when the ultrashort pulsed laser light L3 reaches the specimen A. In addition, even when the wavelength of the ultrashort pulsed laser light L3 selected by the wavelength-selecting optical system 21 is changed, the control unit 25 controls the dispersion-compensating optical system 31 on the basis of the center wavelength of the ultrashort pulsed laser light L3 detected by the spectrometer 24. Therefore, the pulse width of the ultrashort pulsed laser light L3 is also optimized when the ultrashort pulsed laser light L3 reaches the specimen A. Consequently, the multiphoton-excitation effect can be efficiently generated in the specimen A to improve the resolution of multiphoton-excitation images.

Figure 7:
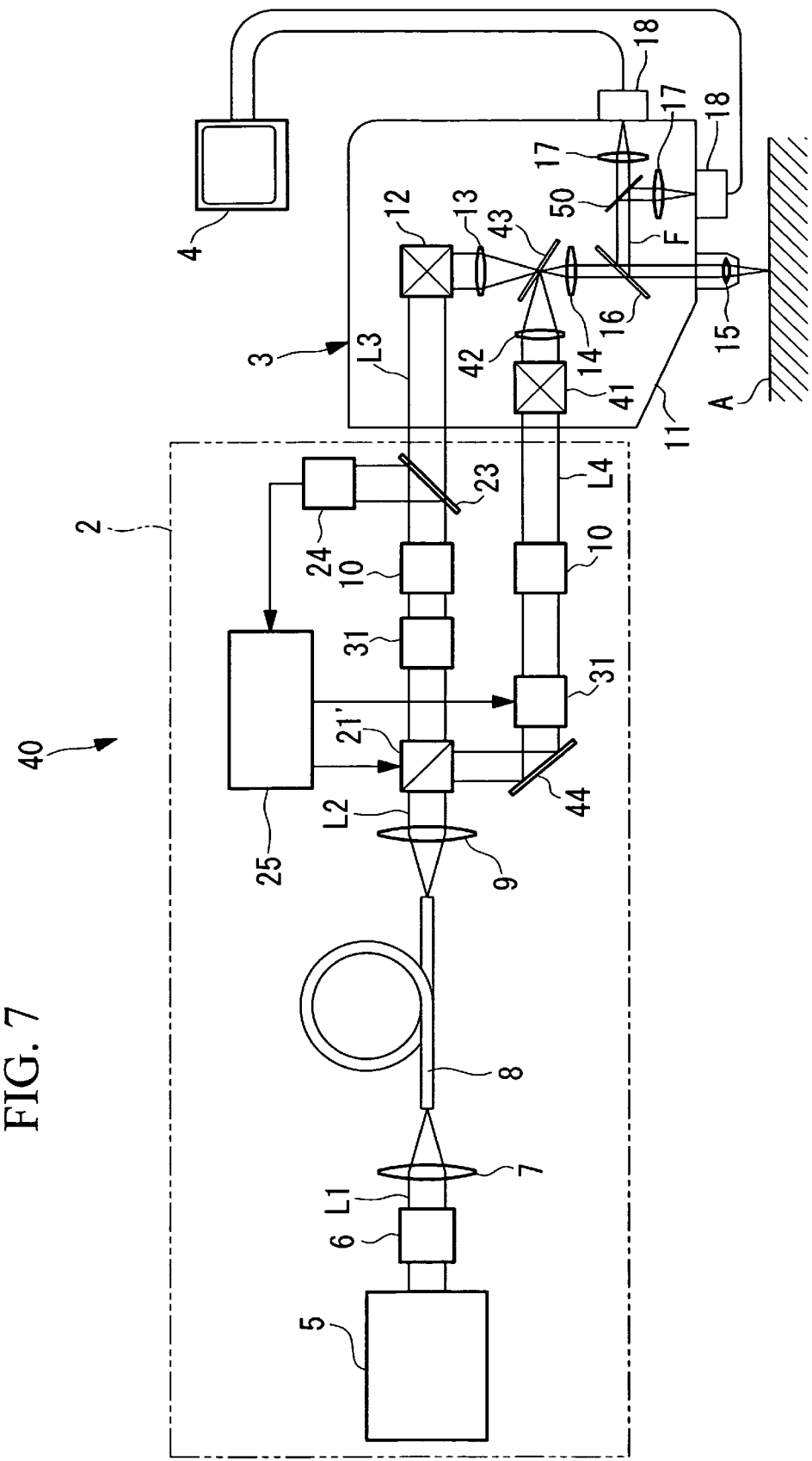
FIG. 7 is an overall structural diagram showing a multiphoton-excitation laser scanning microscope according to a fourth embodiment of the present invention.

A multiphoton-excitation laser scanning microscope 40 according to a fourth embodiment of the present invention will now be described with reference to FIGS. 7 and 8.

In the description of this embodiment, components that are common to those of the above-described multiphoton-excitation laser scanning microscope 20 of the second embodiment have the same reference numerals, and a description of the common structure is omitted.

The multiphoton-excitation laser scanning microscope 40 according to this embodiment includes a wavelength-selecting optical system 21', a second scanner (second laser scanning unit) 41, a pupil-projection lens 42, and a dichroic mirror (multiplexer) 43. The wavelength-selecting optical system 21' separates the white ultrashort pulsed laser light L2 emitted from the collimator optical system 9 into ultrashort pulsed laser light L4 having a predetermined wavelength and remaining ultrashort pulsed laser light L3. The second scanner 41 controls the position of the separated ultrashort pulsed laser light L4 having the predetermined wavelength. The pupil-projection lens 42 focuses the ultrashort pulsed laser light L4 whose position is adjusted by the second scanner 41. The dichroic mirror 43 multiplexes the ultrashort pulsed laser light L4 focused by the pupil-projection lens 42 with the remaining ultrashort pulsed laser light L3 scanned by the scanner 12.

Figure 8:
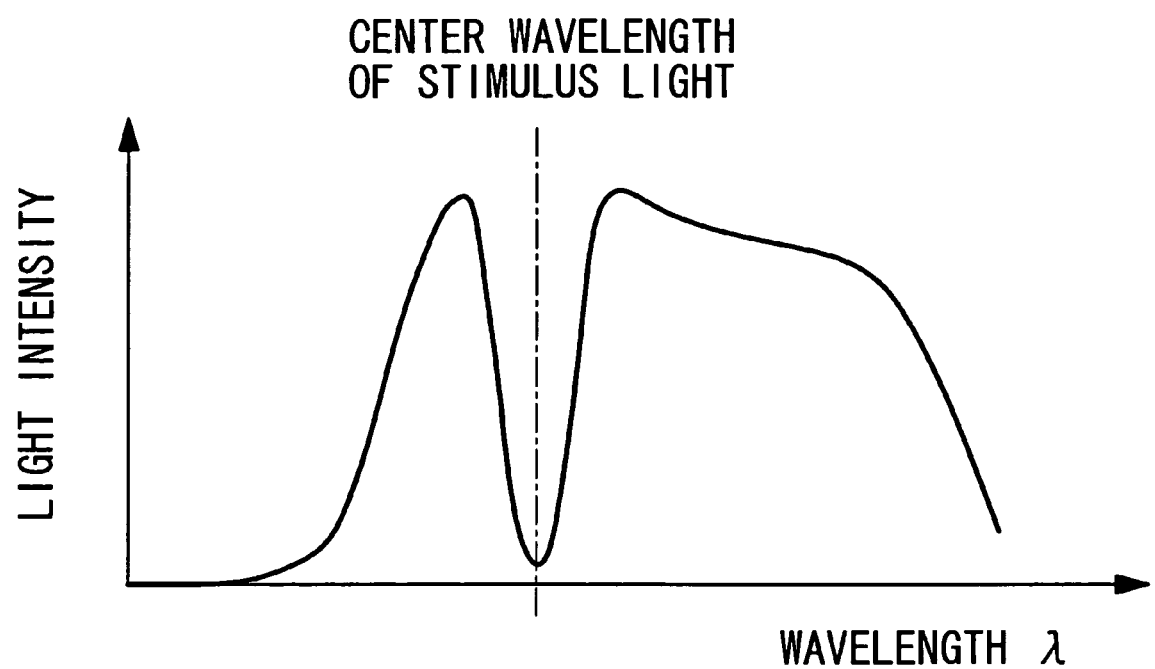
FIG. 8 is graph chart showing the spectrum of remaining ultrashort pulsed laser light obtained by separating ultrashort pulsed laser light having a predetermined wavelength with a wavelength-selecting optical system of the multiphoton-excitation laser scanning microscope in FIG. 7.

In this embodiment, the spectrometer 24 detects the center wavelength of the ultrashort pulsed laser light L4 on the basis of the ultrashort pulsed laser light L3, which has the spectrum shown in FIG. 8, as a result of cutting the ultrashort pulsed laser light L4 having the predetermined wavelength. The control unit 25 controls the wavelength-selecting optical system 21' and the dispersion-compensating optical system 31 disposed on the optical path of the ultrashort pulsed laser light L4 on the basis of the detected center wavelength of the ultrashort pulsed laser light L4. In FIG. 7, reference numeral 44 indicates a mirror.

With the multiphoton-excitation laser scanning microscope 40 according to this embodiment, having the above structure, the white ultrashort pulsed laser light L2, which is spectrally broadened so as to have a spectral range of about 300 to 1,600 nm by passing through the optical fiber 8, passes through the wavelength-selecting optical system 21'. Thereby, the ultrashort pulsed laser light L2 is separated into the ultrashort pulsed laser light L4 having the predetermined wavelength and the remaining ultrashort pulsed laser light L3.

The separated ultrashort pulsed laser light L3 and L4 passes through the corresponding dispersion-compensating optical system 31, thereby compensating for the group velocity dispersions. The ultrashort pulsed laser light L3 and L4 then passes through the corresponding beam-shaping optical system 10, thereby adjusting the beam diameters and the divergences thereof.

As shown in FIG. 8, the ultrashort pulsed laser light L3 split-off by the beam sampler 23 has a spectrum that lacks the part of the cut out ultrashort pulsed laser light L4. Therefore, the center wavelength of the ultrashort pulsed laser light L4 can be easily determined with the spectrometer 24.

Subsequently, the wavelength cut by the wavelength-selecting optical system 21' is adjusted by feeding back the center wavelength of the determined ultrashort pulsed laser light L4. The amount of dispersion compensation of the ultrashort pulsed laser light L4 is adjusted by the dispersion-compensating optical system 31 according to the wavelength.

Accordingly, the ultrashort pulsed laser light L4 is cut by the wavelength-selecting optical system 21' with high accuracy so as to have a desired center wavelength. Furthermore, the group velocity dispersion of the entire microscope that influences the pulse width of the ultrashort pulsed laser light L4 is adequately compensated for by the dispersion-compensating optical system 31 with an amount of dispersion compensation depending on the wavelength. The ultrashort pulsed laser light L4 is introduced into the microscope unit 3 with the beam diameter and the divergence thereof adjusted by the beam-shaping optical system 10.

The ultrashort pulsed laser light L4 thus ideally adjusted is two-dimensionally scanned or two-dimensionally positioned by the second scanner 41. Subsequently, the ultrashort pulsed laser light L4 is irradiated on the specimen A through the pupil-projection lens 42, the dichroic mirror 43, the imaging lens 14, and the objective lens 15.

On the other hand, in the remaining ultrashort pulsed laser light L3 from which the ultrashort pulsed laser light L4 is cut by the wavelength-selecting optical system 21', the group velocity dispersion is adequately compensated for by the dispersion-compensating optical system 31 with an amount of dispersion compensation depending on the wavelength. Furthermore, the ultrashort pulsed laser light L3 is introduced into the microscope unit 3 with the beam diameter and the divergence thereof adjusted by the beam-shaping optical system 10. In the microscope unit 3, the ultrashort pulsed laser light L3 is two-dimensionally scanned by the scanner 12 and is irradiated on the specimen A through the pupil-projection lens 13, the imaging lens 14, and the objective lens 15.

The ultrashort pulsed laser light L3 to be irradiated on the specimen A has a spectrum that lacks the wavelengths of the ultrashort pulsed laser light L4. However, since this ultrashort pulsed laser light L3 includes ultrashort pulsed laser light having a plurality of spectral range, fluorescence by multiphoton excitation F having a plurality of wavelengths can be generated at the same time.

In addition, the ultrashort pulsed laser light L4 to be irradiated on the specimen A has a wavelength that is limited with high accuracy and that is subjected to precise dispersion compensation. Consequently, highly accurate stimulation by multiphoton excitation can be provided to the specimen A.

As described above, according to the multiphoton-excitation laser scanning microscope 40 of this embodiment, the stimulation by multiphoton excitation and the fluorescence by multiphoton excitation observation with a plurality of wavelengths can be performed with a single light source, resulting in a reduction in the product cost. Furthermore, the stimulation by multiphoton excitation and the fluorescence by multiphoton excitation observation with a plurality of wavelengths can be performed with the same timing. This is advantageous in that a phenomenon that instantaneously occurs in the specimen A can be observed without missing it.

In this embodiment, the irradiation position of the ultrashort pulsed laser light L4 on the specimen A is determined by the second scanner 41. Alternatively, by scanning the ultrashort pulsed laser light L4 with the second scanner 41, the stimulation by multiphoton excitation may be provided in a desired area of the specimen A.

In addition, stimulation by single-photon excitation according to the center wavelength selected by the wavelength-selecting optical system 21' can be performed by increasing the pulse width of the ultrashort pulsed laser light L4 with the dispersion-compensating optical system 31.

What is claimed is:

1. A multiphoton-excitation laser scanning microscope comprising:
   a laser light source that emits ultrashort pulsed laser light, wherein the ultrashort pulsed laser light has a pulse width of picosecond-order or shorter, and wherein the ultrashort pulsed laser light has a single wavelength;
   an optical fiber into which the ultrashort pulsed laser light is introduced, wherein the optical fiber broadens a spectrum of the ultrashort pulsed laser light;
   a laser scanning unit that scans the spectrally broadened ultrashort pulsed laser light emitted from the optical fiber;
   an objective optical system that focuses the spectrally broadened ultrashort pulsed laser light scanned by the laser scanning unit onto a focal position in a specimen;
   optical detectors that detect a fluorescence by multiphoton excitation emitted from the focal position in the specimen;
   a dispersion-compensating optical system that compensates for a group velocity dispersion of the multiphoton-excitation laser scanning microscope, wherein the group velocity dispersion influences the pulse width of the ultrashort pulsed laser light;
   a wavelength-selecting optical system that selects a wavelength of the spectrally broadened ultrashort pulsed laser light emitted from the optical fiber;
   a spectrum detecting unit that detects a center wavelength of the ultrashort pulsed laser light whose wavelength is selected by the wavelength-selecting optical system; and
   an adjusting unit that adjusts an amount of the group velocity dispersion compensation based on the center wavelength detected by the spectrum detecting unit.

2. A multiphoton-excitation laser scanning microscope comprising:
   a laser light source that emits ultrashort pulsed laser light, wherein the ultrashort pulsed laser light has a pulse width of picosecond-order or shorter, and wherein the ultrashort pulsed laser light has a single wavelength;
   an optical fiber into which the ultrashort pulsed laser light is introduced, wherein the optical fiber broadens a spectrum of the ultrashort pulsed laser light;
   a wavelength-selecting optical system that selectively separates a predetermined wavelength of the spectrally broadened ultrashort pulsed laser light emitted from the optical fiber;
   a laser scanning unit that scans a remaining portion of the ultrashort pulsed laser light from which the ultrashort pulsed laser light having the predetermined wavelength is separated by the wavelength-selecting optical system;
   a multiplexer that multiplexes the ultrashort pulsed laser light having the predetermined wavelength with the remaining portion of the ultrashort pulsed laser light scanned by the laser scanning unit;
   an objective optical system that focuses the ultrashort pulsed laser light multiplexed by the multiplexer onto a focal position in a specimen; and
   optical detectors that detect a fluorescence by multiphoton excitation emitted from the focal position in the specimen.

3. The multiphoton-excitation laser scanning microscope according to claim 2, further comprising:
   a spectrum detecting unit that detects a center wavelength of the ultrashort pulsed laser light having the predetermined wavelength separated by the wavelength-selecting optical system; and
   a wavelength-adjusting unit that adjusts the predetermined wavelength of the ultrashort pulsed laser light to be separated by the wavelength-selecting optical system based on the center wavelength detected by the spectrum detecting unit.

4. The multiphoton-excitation laser scanning microscope according to claim 3, further comprising:
- a dispersion-compensating optical system that compensates for a group velocity dispersion of the multiphoton-excitation laser scanning microscope, wherein the group velocity dispersion influences the pulse width of the ultrashort pulsed laser light having the predetermined wavelength separated by the wavelength-selecting optical system; and
- a dispersion-compensation adjusting unit that adjusts an amount of the group velocity dispersion compensation based on the center wavelength detected by the spectrum detecting unit.

5. The multiphoton-excitation laser scanning microscope according to claim 2, further comprising:
- a second laser scanning unit that scans the ultrashort pulsed laser light having the predetermined wavelength separated by the wavelength-selecting optical system.

6. The multiphoton-excitation laser scanning microscope according to claim 2, further comprising:
- a peak-intensity-adjusting optical system disposed between the laser light source and the optical fiber, the peak-intensity-adjusting optical system adjusting a peak intensity of the ultrashort pulsed laser light to be introduced into the optical fiber.

7. A multiphoton-excitation laser scanning microscope comprising:
- a laser light source that emits ultrashort pulsed laser light, wherein the ultrashort pulsed laser light has a pulse width of picosecond-order or shorter, and wherein the ultrashort pulsed laser light has a single wavelength;
- an optical fiber into which the ultrashort pulsed laser light is introduced, wherein the optical fiber broadens a spectrum of the ultrashort pulsed laser light;
- a laser scanning unit that scans the spectrally broadened ultrashort pulsed laser light emitted from the optical fiber;
- an objective optical system that focuses the spectrally broadened ultrashort pulsed laser light scanned by the laser scanning unit onto a focal position in a specimen;
- optical detectors that detect a fluorescence by multiphoton excitation emitted from the focal position in the specimen;
- a dispersion-compensating optical system that compensates for a group velocity dispersion of the multiphoton-excitation laser scanning microscope, wherein the group velocity dispersion influences the pulse width of the ultrashort pulsed laser light;
- a wavelength-selecting optical system that selects a wavelength of the spectrally broadened ultrashort pulsed laser light emitted from the optical fiber; and
- an adjusting unit that adjusts an amount of the group velocity dispersion compensation based on the wavelength selected by the wavelength-selecting optical system.

* * * * *